(12) United States Patent
Christofi et al.

(10) Patent No.: US 7,737,191 B2
(45) Date of Patent: Jun. 15, 2010

(54) RUBBER TREATMENT METHOD

(75) Inventors: Nicholas Christofi, Edinburgh (GB); John Geoffrey, Morton (GB); David Edward, Bond (GB)

(73) Assignee: Recyclatech Group Limited, Glasgow (GB)

(*) Notice: Subject to any disclaimer, the term of this patent is extended or adjusted under 35 U.S.C. 154(b) by 633 days.

(21) Appl. No.: 10/546,675

(22) PCT Filed: Feb. 27, 2004

(86) PCT No.: PCT/GB2004/000827

§ 371 (c)(1),
(2), (4) Date: Aug. 22, 2005

(87) PCT Pub. No.: WO2004/076492

PCT Pub. Date: Sep. 10, 2004

(65) Prior Publication Data

US 2006/0293398 A1 Dec. 28, 2006

(30) Foreign Application Priority Data

Feb. 28, 2003 (GB) .................. 0304574.7

(51) Int. Cl.
*C08J 11/04* (2006.01)
(52) U.S. Cl. .................. 521/41; 521/40; 435/262; 435/282
(58) Field of Classification Search ............ 521/40, 521/40.5, 41; 435/262, 282
See application file for complete search history.

(56) References Cited

U.S. PATENT DOCUMENTS

| 5,275,948 A | * | 1/1994 | Straube et al. ............ 435/262 |
| 5,284,195 A | * | 2/1994 | Sandstrom et al. ........ 152/209.5 |
| 5,597,851 A | * | 1/1997 | Romine et al. ............. 521/41 |
| 5,854,058 A |   | 12/1998 | Tsuchii et al. |
| 6,337,204 B1 | * | 1/2002 | Monot et al. .............. 435/282 |
| 6,407,144 B1 | * | 6/2002 | Fliermans et al. ........... 521/41 |
| 7,344,777 B2 | * | 3/2008 | Kino et al. ................. 428/402 |

FOREIGN PATENT DOCUMENTS

| EP | 0 441 462 A | 8/1991 |
| EP | 0 562 313 A | 9/1993 |
| JP | 60072934 | 4/1985 |
| WO | WO 03/048236 | * 6/2003 |

OTHER PUBLICATIONS

Bum et al. International Journal of Systematic Bacteriology (1999), 49, 1845-1851 *Gordonia desulfuricans* sp. nov., a benzothiophene desulfurizing actinomycete.*

Arenskotter, et al., "Taxonomic Characterization of Two Rubber Degrading Bacteria Belonging to the Species *Gordonia polyisoprenivorans* and Analysis of Hyper Variable Regions of 16S rDNA Sequences", *Fems Microbiology Letters*, 205(2):277-282 (2001).

Database WPI, Section Ch, Week 198523, Derwent Publications Ltd., London, GB; AN 1985-137851.

* cited by examiner

*Primary Examiner*—Ling-Siu Choi
*Assistant Examiner*—Frances Tischler
(74) *Attorney, Agent, or Firm*—Daniel A. Monaco; Drinker Biddle & Reath LLP

(57) ABSTRACT

A process and resulting product is provided in which vulcanized rubber crumb has selected chemical bonds broken and sulphur removal by biotreatment with hydrophobic bacteria, such as mycolic acid containing actinomycete bacteria of 'mycolata', without significant degradation of the hydrocarbon polymer. The products obtained from the use of these bacteria may be processed alone or in blends with virgin rubber and revulcanized to yield products of much higher quality than conventional reclaimed rubber materials.

18 Claims, 1 Drawing Sheet a) Natural Rubber (*cis*-1,4-polyisoprene)

b) Synthetic Styrene Butadiene Rubber (SBR)

c) Model Compound- Allyl disulphide

Bond Energies (kJ mole$^{-1}$): C=C, 598; C-C, 349; C-S, 272; S-S, 266; C-H, 372

RUBBER TREATMENT METHOD

The present invention relates to a method of treating rubber. In particular, it relates to a method of treating vulcanised rubber in order that the rubber may be reprocessed or recycled.

BACKGROUND TO THE INVENTION

The largest single application for rubber is in vehicle tyre. The principal rubbers used are the hydrocarbon polymers Natural Rubber (NR), Styrene Butadiene Rubbers (SBR) and Polybutadiene Rubbers (BR). During processing the polymer molecules are vulcanised i.e. cross-linked by sulphur atoms. The formation of cross-links enhances the mechanical properties of the rubber but renders it unsuitable for easy processing. Throughout this application, vulcanised rubber is taken to mean rubber cross-linked by sulphur.

Waste rubber materials, such as vehicle tyres, present a significant environmental problem.

Currently, the European Union scraps a total of nearly $2 \times 10^6$ tonnes of tyres per year of which 23% are retreaded and 46% disposed to landfill. In the UK, it is estimated that approximately 100000 tonnes of tyres are disposed of each year, mainly in landfill sites. In the USA, 300 million tyres are disposed to landfill per annum. In New York State alone, 12 million tyres are discarded per annum, which represents in excess of three million barrels of oil in energy equivalent being discarded.

The United Nations and EU have warned that waste rubber is becoming a significant environmental problem worldwide. The EC Landfill Directive (1999/31/EC) has advocated the banning of disposal to landfill by 2003 for whole tyres and 2006 for shredded tyres.

Currently, alternative means of disposal of waste rubber, in particular waste tyres, include various recycling methods and burning of e.g. in cement kilns. However, burning of rubber materials such as tyres can produce significant pollutants including dioxins.

Life cycle analysis shows that only a small fraction of the energy used in manufacturing tyres is recovered on combustion.

Conventional recycling methods include mechanical, thermo-mechanical, cryomechanical, microwave and ultrasonic methods. Chemical recycling methods include reclamation using organic disulphides, mercaptans and inorganic compounds. However, rubber produced using these methods has poor mechanical properties. There is also pyrolysis of waste rubber to oils and carbon black. Alternative methods of recycling include employing reclaimed rubber that is blended with Low Density Polyethylene (LDPE) to produce mixed polymer elastomeric material. However, rubber produced using these methods has poor mechanical properties.

Rubber crumb is also used in roads, playparks, running tracks and equestrian surfaces. However none of these applications come close to using the large quantities of waste rubber available.

A recent biotechnological approach to recycling rubber involves elastomer recycling to the viscoelastic state by removal of sulphur by the thermophilic bacterium *Sulfolobus*. However, the use of a thermophile at temperatures in the region of 70° carries a large energy cost penalty and generates highly acidic environments with production of sulphuric acid which can lead to reprocessing problems. DE04042009 describes the surface treatment of rubber crumb by suspensions of chemolithotrophic Sulphur-oxidising bacteria allowing revulcanisation to take place when mixed with new (virgin) rubber stock and devulcanisation of comminuted rubber scrap by similar suspensions of chemolithotrophs to produce viscoelastic rubber and sulphuric acid. However, the presence of sulphuric acid in the reaction mixture would be detrimental to revulcanisation and to the quality of any reprocessed rubber.

As current methods of disposal of waste rubber are environmentally unacceptable and conventional methods of recycling produce low quality rubber materials, there remains a need for a method of recycling rubber materials which produces rubber of high quality and reduces environmentally unacceptable consequences.

SUMMARY OF THE INVENTION

The present inventors have surprisingly discovered that hydrophobic bacteria for example mycolic acid containing actinomycete bacteria or 'mycolata' can efficiently devulcanise waste rubber products without causing significant degradation of the unsaturated hydrocarbon polymer forming the rubber chains. The rubber recycled using these bacteria may be revulcanised to produce rubber material of a much higher quality than conventional recycled rubber materials.

DETAILED DESCRIPTION OF THE INVENTION

Figure 1:
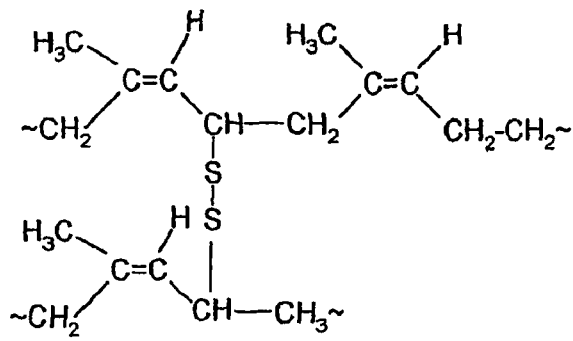
FIG. 1 shows the chemical structures of (a) natural rubber (cis-1,4-polyisoprene, (b) synthetic styrene butadiene rubber (SBR), and (c) the model compound allyl disulphide.
Figure 1:
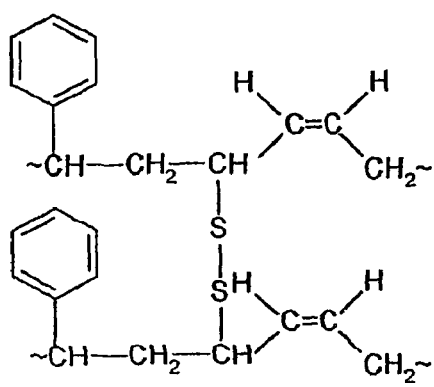
Figure 1:
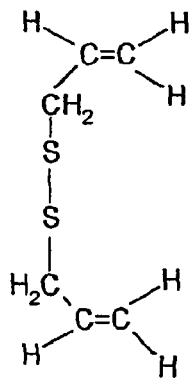

Accordingly, in a first aspect of the present invention, there is provided a method of devulcanising rubber comprising, providing a vulcanised rubber substrate, exposing the vulcanised rubber substrate to mycolata bacteria, and allowing the mycolata bacteria to break down C—S and S—S bonds in the vulcanised rubber substrate to produce a devulcanised rubber.

Throughout this specification, reference to devulcanisation refers to the breaking of C—S and S—S bonds between rubber molecules. Reference to "devulcanised rubber" refers to rubber in which C—S and S—S bonds have been broken.

Preferably, devulcanised rubber produced according to the method of the invention has less than 90%, preferably less than 85%, more preferably less than 80%, even more preferably less than 75%, yet more preferably less than 70%, even more preferably less than 65%, most preferably less than 60% of the C—S and S—S bonds originally present in the "vulcanised" form prior to treatment using the method of the invention. This may be assessed using conventional means of measuring total sulphur content. Preferably, the method of the invention removes at least some sulphur from the rubber substrate. Thus, preferably, devulcanised rubber produced according to the method of the invention has less than 90%, preferably less than 85%, more preferably less than 80%, even more preferably less than 75%, yet more preferably less than 70%, even more preferably less than 65%, most preferably less than 60% of the total sulphur content of the "vulcanised" form prior to treatment using the method of the invention.

Preferably, the devulcanised rubber product produced using the method of the first aspect of the invention is of sufficient quality to be capable of reprocessing and revulcanisation and reprocessing to a new rubber product e.g. rubber tyre, without the need for addition of virgin rubber. However, the recycled rubber is capable of being blended and reprocessed with virgin rubbers in all proportions. Preferably, a tyre produced using such a recycled rubber would meet or exceed the relevant safety and quality standard set for vehicle tyres by UK, EU or US regulatory authorities.

According to a second aspect of the present invention, there is provided a method of recycling a vulcanised rubber comprising devulcanising the rubber according to the first aspect of the invention, and reprocessing the devulcanised rubber. Reprocessing may include blending with virgin rubber and/or may include addition of any further ingredients prior to revulcanisation to yield a high quality rubber product. The reprocessing temperature will generally be sufficient to kill and/or destroy most, preferably all, of the bacteria. Alternatively the devulcanising bacteria can be removed from the rubber by alkali washing prior to further processing.

Examples of mycolata bacteria which may be used in the present invention include, but are not limited to, members of the genera *Corynebacterium, Rhodococcus, Nocardia, Gordonia, Tsukamurella, Dietzia* and *Mycobacterium*. In a preferred embodiment, the bacterium is of the genus *Gordonia*. In a particularly preferred embodiment, the bacteria is the *Gordonia desulfuricans* strain SG213E, samples of which were deposited with the National Collections of Industrial and Marine Bacteria Ltd. (NCIMB), 23 St Machar Drive, Aberdeen, Scotland AB24 3RY on 28 Feb. 2003 and also on 29 Jul. 1996 under accession no NCIMB 40816.

The methods of the invention may be used on any type of vulcanised rubber, in particular waste rubber, such as rubbers used in vehicle tyres. Rubbers for use in the invention may be natural or synthetic or a mixture thereof. Synthetic rubbers include but are not limited to Styrene Butadiene Rubbers (SBR) and Polybutadiene Rubbers (BR). Examples of structural formulae for vulcanised natural rubber, synthetic Styrene Butadiene rubber and the model compound allyl disulphide are shown in FIG. 1.

In order to maximise the surface area of rubber material for reaction with the bacteria, the rubber material is preferably provided in particulate form e.g. such as in the form of rubber crumb, the preparation of which is known to the person skilled in the art. Preferred particle, e.g. crumb, sizes are in the range 0.1 mm to 15 mm, for example 1 mm to 15 mm. Such particles, e.g. crumbs, may be formed using any method known in the art, for example mechanical and/or cryogenic grinding.

Moreover, the present inventors have found that the efficiency of the methods of the invention and the quality of the devulcanised rubber produced using the methods of the invention may be enhanced by carrying out the reaction in the presence of rubber processing oils such as hydrocarbon oils, and similar materials which contain long hydrocarbon sequences in the molecular structure e.g. stearic acid. In a preferred embodiment the rubber processing oil is stearic acid. In a further preferred embodiment, the rubber processing oil is hexadecane.

Without being limited to a particular mechanism it is believed that by coating the rubber particles with such oils, or similar materials, the surface area on which the bacteria may act is increased and access to the C—S and S—S bonds is improved, enabling more efficient breaking of the C—S and S—S bonds and preferably removal of sulphur to leave a devulcanised rubber. Moreover, by coating the rubber particles in such oil, or similar materials, the bacteria may use the oil as a Carbon source for growth instead of using the rubber hydrocarbon polymer, thus further limiting the degradation of the rubber hydrocarbon chains. Accordingly, in particularly preferred embodiments of the invention, the rubber material e.g. in the form of rubber crumb, is reacted with bacteria in the presence of oils, or similar materials, which can act as carbon sources for the devulcanising bacteria. Suitable oils include but are not limited to mineral oils such as paraffinic, naphthenic, aromatic and white oils. Particularly preferred for use in the methods of the invention are oils which allow swelling of the rubber with greater access to sulphur cross-links. In addition, the metabolism of such rubber processing oils which may be used by the bacteria in the methods may result in the production of surface active agents (surfactants) which further enable access of the bacteria to the sulphide bridges.

Although any suitable temperature range may be used in the methods of the invention, the temperature being determined principally by the optimum temperature required for activity of the particular bacteria being used, in preferred embodiments the bacteria are active in breaking the C—S bonds and S—S bonds at mesophilic temperature ranges, e.g. in the range 15-40° C., preferably in the range 20-35° C. The use of bacteria which devulcanise rubber products at room temperature enables gentler treatment of the rubber products compared to conventional treatments to reclaim rubber, many of which require treatment at high temperatures. The use of mesophilic bacteria enables the breakdown of C—S and S—S bonds between the unsaturated "rubber" hydrocarbon polymer chains, which constitute the main rubber chains, without degrading the hydrocarbon polymer.

In preferred embodiments, the method is carried out under conditions of pH in the range pH5 to pH9, preferably in the range pH6 to pH8, most preferably at around pH 7 i.e. in the range pH 6.5 to pH 7.5. Preferably, the method is performed under aerobic conditions.

The methods of the invention may be carried out in any suitable reaction vessel, including biopiles, preferably with means for controlling reaction conditions. Various reaction conditions and factors maybe modified in order to control the rate and extent of bacterial devulcanisation according to the method of the invention. For example, the rate and/or extent of bacterial devulcanisation of rubber product may be controlled by controlling one or more of oxygen tension, redox potential, temperature, process oil concentration, mixing speed during devulcanisation, and/or physical and/or chemical treatment of the rubber substrate e.g. rubber crumb prior to devulcanisation according to the method of the invention.

The rubber material may thus be pre-treated prior to reaction with the bacteria. Such pre-treatments may include method steps to at least partially remove textile fibres, metal beads and other constituents in the vulcanised rubber as well as chemical and/or mechanical treatments.

Preferably, during reaction, the reaction mixture of rubber and bacteria are agitated together, e.g. using a rotating drum. Mixing speed may be adjusted to provide control of the rate of reaction.

In preferred embodiments of the invention, the method is carried out under conditions of undetectable or very low sulphur concentration e.g. less than 0.025%, preferably less than 0.01% sulphur such that the bacteria degrade the sulphur bonds between the rubber molecules to utilise the sulphur in the vulcanised rubber causing devulcanisation. Preferably the method is carried out whereby all trace elements necessary for the growth of the bacteria are present except for sulphur, The incubation time of bacteria with the rubber substrate according to the method of the invention may be adjusted dependent on a number of factors including particular bacteria used, temperature of reaction, size of rubber substrate particles used, presence and nature of carbon support. Typically, the rubber substrate will be incubated with the bacteria for an incubation time in the range 1 to 96 hours or longer.

In preferred embodiments, the oxygen tension may be in the range 0.5-20 mg/L, for example 2-20 mg/L. More preferably, the oxygen tension is in the range 0.5-9.0 mg/L. Most preferably the oxygen tension is 4-8 mg/L. The oxygen tension may however be higher depending on the system internal pressure.

Following treatment, the devulcanised rubber may be washed and filtered in order to remove any residual bacteria. Additionally or alternatively, any live residual bacteria may be killed by reprocessing the rubber at high temperatures. For example, reprocessing of the devulcanised rubber will typically take place at temperatures in excess of 100° C., for example 150° C., which will kill bacteria such as the mycolata which are preferred for use in the methods of the invention.

In a further aspect of the invention there is provided devulcanised rubber produced according to the methods of the invention.

Devulcanised rubber of the invention and made according to the present invention has superior properties to recycled rubber produced according to conventional methods and may be revulcanised and used in the production of new rubber products, for example in the production of tyres. The quality of rubber produced by the methods of the invention may be tested using conventional rubber quality criteria known to those versed in the art. Such criteria include plasticity (e.g. ASTM Standard D1646), scorch (e.g. ASTM Standard D1646), minimum viscosity (e.g. ASTM Standard D1646), shore hardness (e.g. ASTM Standard D2240), modulus of elongation at 300% and 100% (e.g. ASTM Standard D412, test method A), elongation at break (e.g. ASTM Standard D412, test method A), energy at break (e.g. ASTM Standard D412, test method A as set forth in units of MPa), G' (e.g. ASTM Standard D2221) and Tan Delta hysteresis measured in accordance with ASTM Standard Db 2231 ).

The invention will now be exemplified with reference to the following non-limiting description and the accompanying FIG. 1, which shows structural formulae of some vulcanised rubber molecules.

EXAMPLES

Using old tyres, rubber crumb is prepared and treated with process oil such as one or more mineral oils such as paraffinic, naphthenic, aromatic or white oil in a reaction vessel. A bacterial suspension of *Gordonia desulfuricans* strain SG213E (NCIMB 40816 or as deposited with NCIMB on Feb. 28, 2003) is mixed with the rubber crumb and process oil at room temperature (20-30° C.) for a period of 2-12 days, but preferably 4-7 days. The presence of the oil swells the rubber crumbs, allowing enhanced access of the bacteria to C—S and S—S bonds, while protecting the rubber hydrocarbon chains from degradation by acting as a C source for the bacteria. Temperature, aeration, crumb mass to process oil ratio, and other physico-chemical factors are controlled to optimise reaction conditions.

After reaction, the devulcanised rubber is recovered from the reaction vessel, filtered and washed and tested for extent of devulcanisation and quality of rubber product using tests known in the art. Suitable properties of the rubber product which may be tested include one or more of tensile strength, modulus, hardness, tear resistance and solvent swelling of the recovered rubber. Tests for the appearance of inorganic sulphur in the process effluent or liquid residue may also be carried out, as well as total sulphur content of the rubber.

In addition, periodically during the reaction period, samples may be removed from the reaction vessel and tested for extent of devulcanisation and product quality using one or more of such tests.

Example 1

50 g of 12 mesh rubber crumb derived from truck tyres was rotated in a horizontal cylindrical vessel with 100 cm³ of aqueous medium containing essential minerals, between 0.1 and 3 cm³ of hexadecane and 500 µl innoculum of a late logarithmic growth phase culture of *Gordonia desulfuricans* (NCIMB 40816) grown in a similar medium supplemented with benzothiophene as a sulphur source.

Typical aqueous medium composition in gdm⁻³
$Na_2HPO_4$ 4.33 g, $KH_2PO_4$ 2.65 g, $NH_4Cl$ 2 g,
$MgCl_2.6H_2O$ 0.64 g, $CaCl_2.2H_2O$ 33 mg, $ZnCl_2$ 2.6 mg,
$FeCl_2.4H_2O$ 2.6 mg, EDTA 1.25 mg, $MnCl_2.4H_2O$ 1 mg, $CuCl_2.2H_2O$ 0.15 mg,
$Co(NO_3)_2.6H_2O$ 0.125 mg,
$Na_2B_4O_7.10H_2O$ 0.1 mg, $(NH_4)_6Mo_7O_{24}.4H_2O$ 0.09 mg.

The medium was changed when maximum growth of the bacteria was observed. This change could be repeated several times. The percentage reduction of total sulphur content in the rubber samples after treatment varied between 23% and 35%.

When blended with virgin rubber stock at a loading of 40% by weight and revulcanised, the treated crumb samples showed good tensile strength substantially higher than similar vulcanised blends containing untreated crumb. Eg
Blend with 40% treated crumb, 20.9 MPa
Blend with 40% untreated crumb, 17.1 Mpa

Example 2

The same process was carried out as in Example 1 but with hexadecane is replaced by glycerol. In contrast to example 1 when hexadecane is replaced by glycerol as a carbon support there is no significant reduction in the total sulphur content of the rubber.

Example 3

The same process was carried out as in Example 1 but with *Gordonia desulfuricans* replaced by a *Rhodococcus erythropolis* strain DT10. In contrast to example 1, the reduction in total sulphur content of the rubber was substantially lower at 13%.

Example 4

The same process was carried out as in Example 1 but with *Gordonia desulfuricans* replaced by the *Rhodococcus erythropolis* strain used in example 3 and the hexadecane replaced by glycerol. In contrast to example 1 there was no significant reduction in total sulphur content of the rubber.

Example 5

The same process was carried out as in Example 1 but with *Gordonia desulfuricans* is replaced by a further *Rhodococcus erythropolis* strain. in contrast to example 1 when *Gordonia desulfuricans* was replaced by a further *Rhodococcus erythropolis* strain DT05, the reduction in total sulphur content of the rubber was 11%.

Example 6

The same process was carried out as in Example 1 but with *Gordonia desulfuricans* replaced by the same strain of *Rhodoccocus erythropolis* as used in example 5 and hexadecane replaced by glycerol. In contrast to example 1 the reduction in total sulphur content of the rubber was only 9%.

All documents referred to in this specification are herein incorporated by reference. Various modifications and variations to the described embodiments of the inventions will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the art are intended to be covered by the present invention.

The invention claimed is:

1. A method of devulcanising rubber comprising providing a vulcanised rubber substrate, exposing the vulcanised rubber substrate to mycolata bacteria, and allowing the mycolata bacteria to break down C—S and S—S bonds in the vulcanised rubber substrate to produce a devulcanised rubber, wherein the mycolata bacteria comprise a bacteria *Gordonia desulfuricans*.

2. The method according to claim 1, wherein the devulcanised rubber has less than 95% of the C—S and S—S bonds originally present in the vulcanised rubber substrate.

3. The method according to claim 2, wherein the devulcanised has less than 70% of the C—S and S—S bonds present in the vulcanised rubber substrate.

4. The method according to claim 1, wherein the devulcanised rubber has less than 90% of the total sulphur content of the vulcanised rubber substrate.

5. The method according to claim 1, wherein the *Gordonia desulfuricans* bacteria comprise *Gordonia desulfuricans* strain SG213E (accession no: NCIMB 40816).

6. The method according to claim 1, wherein the rubber substrate is in particulate from, wherein the particles have a cross section in the range 0.1 mm to 15 mm.

7. The method according to claim 1, wherein the rubber substrate is exposed to the mycolata bacteria in the presence of one or more processing oils.

8. The method according to claim 7, wherein the processing oil is stearic acid or hexadecane.

9. The method according to claim 1, wherein the method is performed at a temperature in the range 15-40° C.

10. The method according to claim 1, wherein the method is performed under conditions of less than 0.025% sulphur.

11. The method according to claim 1, wherein the method is performed under conditions of oxygen tension in the range 0.5-9.0 mg/L.

12. A method of recycling vulcanised rubber comprising devulcanising vulcanised rubber according to the devulcanising method of claim 1 and revulcanising the rubber product to produce a recycled rubber product.

13. The method according to claim 12, wherein the devulcanised rubber is reprocessed at a temperature of greater than 100° C.

14. The method according to claim 12 comprising the step of forming a tire using the recycled rubber product.

15. A devulcanised rubber produced according to the method of claim 1.

16. A recycled rubber product produced according to the method of claim 12.

17. A tire comprising recycled rubber product produced according to the method of claim 12.

18. A tire produced according to the method of claim 14.

* * * * *